(12) United States Patent
Sobek et al.

(10) Patent No.: US 7,704,360 B2
(45) Date of Patent: Apr. 27, 2010

(54) DEVICES AND METHODS FOR SEPARATING SAMPLE CONSTITUENTS

(75) Inventors: Daniel Sobek, Loveland, CO (US); Christian A. Heid, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 1403 days.

(21) Appl. No.: 11/080,282

(22) Filed: Mar. 14, 2005

(65) Prior Publication Data

US 2006/0201807 A1 Sep. 14, 2006

(51) Int. Cl.
*B01D 57/02* (2006.01)
(52) U.S. Cl. .................. 204/450; 204/601; 204/606; 204/451; 200/451; 200/450
(58) Field of Classification Search ............... 204/450, 204/451, 601, 606; 200/450, 451
See application file for complete search history.

(56) References Cited

U.S. PATENT DOCUMENTS

| 5,320,727 | A | 6/1994 | Jackson |
| 6,254,754 | B1 | 7/2001 | Ross et al. |
| 6,296,752 | B1 * | 10/2001 | McBride et al. ............. 204/547 |
| 6,537,432 | B1 | 3/2003 | Schneider et al. |
| 6,638,408 | B1 * | 10/2003 | Speicher et al. ............. 204/458 |
| 7,041,208 | B2 * | 5/2006 | Staats ........................ 204/455 |
| 2004/0115725 | A1 | 6/2004 | Pieper et al. |

* cited by examiner

*Primary Examiner*—Jennifer K Michener
*Assistant Examiner*—Xiuyu Tai (57) ABSTRACT

Devices and methods for separating sample constituents are provided. The subject devices are characterized by having a fluid flow path with at least one electrophoretic separation element positioned at a region thereof. The separation element includes an element for applying an electric field across the fluid flow path and a trapping element for trapping sample constituents that migrate out of the flow path when an electric field is applied across the fluid flow path. In using the subject devices, sample is moved past the separation element and an electric field is applied across the flow path such that constituents of the sample migrate into the trapping element. The subject devices and methods find use in a variety of applications, including protein separation applications.

18 Claims, 3 Drawing Sheets

DEVICES AND METHODS FOR SEPARATING SAMPLE CONSTITUENTS

INTRODUCTION

The study of life sciences involves classification and characterization of a variety of biomolecules. The study of proteins is ubiquitous in life sciences and many techniques have been used to isolate, separate and characterize proteins from a variety of sources. Established techniques for protein separation include electrophoresis and liquid chromatography. Traditionally electrophoretic techniques have been used to separate and characterize proteins. Proteins, in common with the majority of biomolecules, are charged or can be made to be charged by defining the media in which they are present. Consequently they will move, in solution, under the influence of an electric field with a velocity which is dependent on the charge to mass ratio of the protein; when the molecule has no charge it has no mobility.

Two traditional electrophoretic techniques for protein separation are isoelectric focusing (IEF) and SDS-PAGE.

IEF separates proteins on the basis of their isoelectric point. Most proteins carry a number of charged or chargeable side chains in addition to the N- and C-terminal moieties that are also capable of carrying a charge. Depending on the pH of the buffer in which the protein is contained, these chargeable groups will carry a 0 to +1 charge if it is an amine function, and −1 to 0 charge if it is an acid group. Since the degree of ionization will also depend on local environment, this will result in a number of different degrees of charged states over the entire protein. At a particular and idiosyncratic pH, the mixture of positive and negative charges will balance and the protein will have a net charge of 0. This property can be harnessed to separate proteins on the basis of the pH at which their net charge is zero. This pH is referred to as the isoelectric point or pI of the protein.

IEF may be operated by constructing a pH gradient between two electrodes with the highest pH at the negative electrode (cathode) and lowest pH at the positive electrode (anode). A pH gradient may be created using a complex mixture of chemicals called ampholytes. These will arrange themselves between the anode and cathode such that they create a gradient of increasing pH from the anode to the cathode. When proteins are introduced into this system, their charge will depend on the pH of the environment in which they find themselves. If the environmental pH is lower than the protein's pI, then it will have a net positive charge and will migrate towards the negative electrode. In this direction, the pH increases and the protein's net charge will become zero when the local pH is the same as its pI. Any further movement via diffusion in the direction of the negative electrode will expose the protein to a pH higher than its pI and at this point its net charge will become negative and vice versa. The protein will then migrate back towards the positive electrode until it focuses into the pH region equal to its pI. In this way, the proteins will focus in different areas depending upon their isoelectric points and this technique allows separation on the basis of pI. Such separations may be conveniently carried out in a supportive media, e.g., in a gel or in a capillary format.

A second technique for separating proteins is to separate them on the basis of their size. This can also be achieved using electrophoretic phenomena. In these separation protocols, proteins may be separated by causing them to migrate through a sieving structure, such as one produced by making a cross-linked gel or a solution of entangled polymers. In such applications, small protein molecules will travel faster than large protein molecules and any mixture of these will therefore separate according to molecular weight. In certain applications, the proteins are treated with an agent, such as sodium dodecyl sulfate or SDS, which imparts to the proteins a substantially constant charge to size ratio.

In certain applications, the above two techniques are combined to provide a separation of a complex mixture of proteins firstly in one dimension by IEF and secondly by SDS-protein sieving. The combination of two separation selectivities in orthogonal directions provides a powerful way of separating very complex mixtures or of characterizing a protein product, and is known in the art as two dimension protein separation.

There is continued interest in the development of methods of separating sample constituents, and particularly protein constituents.

SUMMARY OF THE INVENTION

Devices and methods for separating sample constituents are provided. The subject devices are characterized by having a fluid flow path with at least one electrophoretic separation element positioned at a region thereof. The separation element includes an element for applying an electric field across the fluid flow path and a trapping element for trapping sample constituents that migrate out of the flow path when an electric field is applied across the fluid flow path. In using the subject devices, sample is moved past the separation element and an electric field is applied across the flow path such that constituents of the sample migrate into the trapping element. Movement of sample along the flow path and application of an electric field across the flow path may occur sequentially or simultaneously. The subject devices and methods find use in a variety of applications, including protein separation applications.

DEFINITIONS

Unless defined otherwise, all technical and scientific terms used herein have the same meaning as commonly understood by one of ordinary skill in the art to which this invention belongs. For the sake of clarity and ease of reference, certain elements are defined below.

As used herein, the terms protein, peptide and polypeptide are used interchangeably and refer to a polymer of amino acid residues. The term also applies to amino acid polymers in which one or more amino acids are chemical analogues of corresponding naturally-occurring amino acids, including amino acids which are modified by post-translational processes (e.g., glycosylation and phosphorylation).

The term "separating" refers to physically dividing two initially combined entities.

As used herein, the term "determining" means to identify, i.e., establishing, ascertaining, evaluating or measuring, a value for a particular parameter of interest. The determination of the value may be qualitative (e.g., presence or absence) or quantitative, where a quantitative determination may be either relative (i.e., a value whose units are relative to a control (i.e., reference value) or absolute (e.g., where a number of actual molecules is determined).

As used herein, the term "detecting" means to ascertain a signal or event, e.g., passage of a protein band past a point in space, either qualitatively or quantitatively.

The term "sample" as used herein refers to a fluid composition, where in certain embodiments the fluid composition is an aqueous composition.

The term "capillary" as used in reference to an electrophoretic device in which electrophoresis is carried out in the methods of the invention is used for the sake of convenience. The term should not be construed to limit the particular shape of the cavity or device in which electrophoresis is conducted. In particular, the cavity need not be cylindrical in shape. The term "capillary" as used herein with regard to any electrophoretic method includes other shapes wherein the internal dimensions between at least one set of opposing faces are approximately 2 to 1000 microns, and more typically 25 to 250 microns. An example of a non-tubular arrangement that can be used in certain methods of the invention is a Hele-Shaw flow cell, known in the art. Further, the capillary need not be linear; in some instances, the capillary is wound into a spiral configuration, for example.

The terms "reference" and "control" are used herein interchangeably to refer to a set of values against which a set of experimentally obtained values may be compared to determine a hybridization pattern of interest.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any of the currently available computer-based systems are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

DETAILED DESCRIPTION OF THE INVENTION

Devices and methods for separating sample constituents are provided. The subject devices are characterized by having a fluid flow path with at least one electrophoretic separation element positioned at a region thereof. The separation element includes an element for applying an electric field across the fluid flow path and a trapping element for trapping sample constituents that migrate out of the flow path when an electric field is applied across the fluid flow path. In using the subject devices, sample is moved past the separation element and an electric field is applied across the flow path such that constituents of the sample migrate into the trapping element. The subject devices and methods find use in a variety of applications, including protein separation applications.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described. Methods recited herein may be carried out in any order of the recited events which is logically possible, as well as the recited order of events.

All patents and other references cited in this application, are incorporated into this application by reference except insofar as they may conflict with the definitions of the present application (in which case the present application prevails). The citation of any publication is for its disclosure prior to the filing date and should not be construed as an admission that the present invention is not entitled to antedate such publication by virtue of prior invention.

In further describing the subject invention, representative devices are reviewed first in greater detail, followed by a discussion of the subject methods and representative applications in which the devices and methods find use.

Devices

As summarized above, the present invention provides devices for separating constituents of a sample. The devices are electrophoretic devices, by which is meant that the devices effect separation of sample constituents at least partially by use of an applied electric field, as described in greater detail below. A feature of the subject devices is that they include a fluid flow path and at least one electrophoretic separation element positioned at a location (i.e., region) along the fluid flow path. In further describing the subject devices, aspects of the devices will be reviewed first in greater detail in general terms, followed by a review of representative embodiments with respect to the figures thereof provided in the application.

The fluid flow path of the device is an elongated structure having at least one fluid port that provides for fluid communication between the inside of the path and the external environment of the device, either directly or through a suitable fluid communication element, e.g., conduit. In certain embodiments, the fluid flow path includes a fluid entry port and a fluid exit port, where the ports may be positioned at any location along the fluid flow path, but in certain embodiments are positioned at or near the ends of the flow path. The fluid flow path is, in representative embodiments, an enclosed flow path. The fluid flow path may have a variety of configurations, including tube-like, trench-like or other convenient configuration, where the cross-sectional shape of the flowpath may be circular, ellipsoid, square, rectangular, triangular and the like. The flow path, which may also be viewed as a channel, may be straight, curved or another convenient configuration, as desired. The dimensions of the fluid flow path may vary, where in representative embodiments the fluid flow path may have at least one of the cross-sectional dimensions, e.g., width, height, diameter, ranging in length from about as small as 10 microns to about 1.5 mm or more, where additional representative ranges for certain embodiments are provided below. The overall length of the flow path may also vary, and in representative embodiments may range from as short as about 2 to 3 mm or shorter (including as short as about 1 mm or shorter, such as 0.5 mm or shorter, e.g., 0.25 mm or shorter, including 0.1 mm or shorter, up to about 20 cm or longer, e.g., 25 cm or longer.

Positioned at a region, i.e., defined location or site, of the flow path is an electrophoretic separation element. The electrophoretic separation element includes: (1) a element for applying an electric field, e.g., in the form of a potential difference or voltage, across the flow path at the region of the separation element; and (2) a trapping element for retaining constituents of a sample that migrate out of the flow path under the influence of the applied electric field. A feature of the electrophoretic separation element, and flow path region associate therewith, is that the pH is capable of being precisely controlled therein, such that during use the separation element and associated region of the flowpath traversed thereby have a defined pH, and does not include a pH gradient.

The element for applying electric field (i.e., electric field application element) may take any configuration that is sufficient to produce an electric field across the flow path at the region of the separation element between the trapping element and a site of the flow path opposite the trapping element. In representative embodiments, the trapping element is in conductive communication with a first electrode (or pluralities of electrodes, depending the on the particular device configuration) and the site of the flow path opposite the trapping element is in conductive communication with a second electrode. In representative embodiments, the first electrode(s) in conductive communication with the trapping element is maintained at a positive bias, while the second electrode is grounded or maintained at a negative bias. The electrodes employed in the subject devices may be any convenient type capable of applying an appropriate electric field to the medium present in the electrophoretic flowpath with which they are associated.

The electric field application element is one that applies an electric field across the flow path. In representative embodiments, the direction of the applied electric field is orthogonal, or at least substantially orthogonal, to the direction of fluid flow along the fluid flow path. The direction of fluid flow in the flow path is considered to be the direction of bulk fluid flow going from the beginning to the end of the flow path. Where the electric field has a direction that is substantially orthogonal but not truly orthognal or normal to the direction of fluid flow in the flow path (e.g., which direction is the same as the longitudinal axis of a linear flow path), the deviation from 90° or normal of the electric field relative to the direction of fluid flow at the intersection does not exceed about 40°, and in certain embodiments does not exceed about 30°, including about 20°, about 15°, about 10°, or about 5°.

The trapping element of the electrophoretic separation element serves to retain sample constituents that migrate out of the flow path when an electric field is applied across the flow path at the region of the separation element. The trapping element may take any convenient configuration, so long at it is capable of retaining sample constituents that migrate out of the flow path. In certain embodiments, the trapping element is configured as a compartment separated from the flow path by an ion permeable membrane that is permeable to molecules having a size that ranges from about 1000 daltons to about $10^7$ daltons or more. The compartment of the trapping element may include a gel composition that serves to trap molecules migrating into the trapping element, where the gel composition may be charged with a fixed charge, as desired.

In certain embodiments, the gel composition of the trapping element is a gel employed in electrophoretic applications, i.e., it is an electrophoretic gel medium. Any convenient electrophoretic gel medium may be present on the trapping element. Electrophoretic gel media suitable for use, depending on the particular application, include crosslinked and uncrosslinked polymeric media, and the like, as disclosed in Barron & Blanch, "DNA Separations by Slab Gel and Capillary Electrophoresis: Theory and Practice," Separation and Purification Methods (1995) 24:1-118, as well as U.S. Pat. No. 5,569,314 the disclosure of which is herein incorporated by reference. Of particular interest as electrophoretic gel media are cellulose derivatives, polyacrylamides, polyvinyl alcohols, polyethylene oxides, and the like.

In certain embodiments, the trapping element includes a size separation gel. Gel media providing for a diversity of different sieving capabilities are known. By varying the pore size of the media, employing two or more gel media of different porosity, and/or providing for a pore size gradient, an appropriate size separation gel may be provided in the trapping element. In such embodiments, two or more different electrodes may be in conductive communication with the size separation gel present in the trapping element, such that an electric field can be applied across the size separation gel, e.g., to effect size separation of constituents present in the gel of the trapping element.

In representative embodiments, the electrophoretic separation element(s) of the devices include first and second opposing compartments separated from each other by the fluid flow path. The first and second compartments are separated from the fluid flow path by barriers, e.g., membranes or analogous structures, where the barrier separating the second compartment from the fluid flow path is one that is permeable only to ions and molecules that do not exceed about 1000 daltons, such as about 100 daltons, and the barrier separating the first compartment (i.e., the trapping element, as described above) from the fluid flow channel is one that is permeable to ions as well as larger entities, e.g., small and large molecules, including macromolecules, e.g., peptides and proteins, e.g., as described above, e.g., entities up to 200,000 daltons or more. Any convenient structure may be employed as the barriers separating the compartments of the separation element from the flow path, where representative barriers of interest include ion permeable membranes that may or may not also be permeable to larger molecules. Such membranes are available from a number of commercial vendors, e.g., Millipore, Pall, etc. In these representative configurations, the first and second compartments of the separation elements may have a variety of different configurations, e.g., cubic, spheroid, etc., as convenient, and may vary with respect to volume.

In certain embodiments, the subject devices include two or more distinct electrophoretic separation elements sequentially positioned along the flow path. In such embodiments, the total number of electrophoretic separation elements positioned along the flow path may vary, ranging from about 2 to about 100 or more, but in representative embodiments ranges from about 2 to about 50, such as from about 5 to about 25, e.g., 5 to about 15. In such embodiments, the spacing between any two given separation elements may vary, and is chosen such that the residence time of the fluid in the inter-separation region, i.e., region between two given electrophoretic separation elements, can be pH modulated as desired, where the length of inter-separation element, i.e., spacing between electrophoretic separation elements, may be chosen in view of flow rate, channel dimensions, mixing, e.g., via diffusion or active mixing, etc., but is sometimes at least about 100 microns long, such as at least about 200 microns long or longer, e.g., up to about 1 mm or more, including up to about 5 mm or more.

In certain of these embodiments, located between any two given electrophoretic separation elements is a pH adjustment element. The pH adjustment element may be any element that can increase or decrease, as desired, the pH of fluid in the flow path between the two separation elements. In certain embodiments, the pH adjustment element may be a fluid conduit that opens into the flow path and provides for introduction into the flow path of a fluid that modulates the pH of the fluid in the flow path, e.g., a fluid that is acidic or alkaline with respect to the fluid in the flow path at the site of fluid introduction. In certain embodiments, the pH adjustment element may include a fluid mixing element, which element applies agitation to fluid in the flow path to ensure efficient combination of the pH adjustment fluid and the sample in the flow path. The pH adjustment elements may be configured to provide a defined stepwise change, e.g., increase, in pH along the flow path. As such, during use of the subject devices, a discontinuous pH gradient of regions of increasing pH may be produced in the flow path, where pH gradient is not continuous, as is observed in many isoelectric focusing devices where ampholytes or analogous mediums are employed to produce a continuous pH gradient.

The flow path may optionally comprise fluid reservoirs at one or both termini, i.e., either end, of the flowpath. Where reservoirs are provided, they may serve a variety of purposes, such as a means for introducing sample into the flowpath, removing sample constituents from the flowpath, and the like.

The subject devices may also optionally comprise an interface means for assisting in the introduction of sample into or out of the flow path. For example, where the sample is to be introduced by syringe into the device, the device may comprise a syringe interface which serves as a guide for the syringe needle into the device, as a seal, and the like.

In certain embodiments, the device is a microfluidic device, such that at least the fluid flow path of the device is of microfluidic dimensions, e.g., such as the dimensions of a capillary, as defined above. In certain embodiments, the device is an integrated microfluidic device. By integrated is meant that the configuration of the device elements is such that the device is presented as a single structure, e.g., a chip or analogous microfluid integrated structure. The integrated device may have any convenient configuration capable of providing the flow path and separation elements. In certain embodiments, the flowpath and separation elements may be present on the surface of a planar substrate, where the substrate may be covered with a planar cover plate to seal the flow path and separation elements present on the surface from the environment. In such embodiments, the devices may be small, having a longest dimension in the surface plane of no more than about 200 mm, such as no more than about 100 mm so that the devices may be readily handled and manipulated. The devices of such embodiments may have a variety of configurations, including parallelepiped, e.g., credit card or chip like, disk like, syringe like or any other compact, convenient configuration.

More specifically, the flow paths of capillary dimension are part of or formed within a substrate to form a part of a microfluidic device that can be used to conduct the analyses of the invention on a very small scale and with the need for only minimal quantities of sample. Methods for fabricating and moving samples within microfluidic channels or capillaries and a variety of different designs have been discussed including, for example, U.S. Pat. Nos. 5,858,188; 5,935,401; 6,007,690; 5,876,675; 6,001,231; and 5,976,336, all of which are incorporated by reference in their entirety. Other components necessary for conducting an electrophoretic analysis can be etched into the support, including for example the reservoirs, detectors and valves, etc., as is known in the art.

The substrate upon which the capillary or micro-channel network of the analytical devices of the present invention are formed can be fabricated from a wide variety of materials, including silicon, glass, fused silica, crystalline quartz, fused quartz and various plastics, and the like. Other components of the device (e.g., detectors and microfluidic valves) can be fabricated from the same or different materials, depending on the particular use of the device, economic concerns, solvent compatibility, optical clarity, mechanical strength and other structural concerns. Generally, the substrate is manufactured of a non-conductive material to allow relatively high electric fields to be applied to electrokinetically transport the samples through the various channels.

In the case of polymeric substrates such as plastics, the substrate materials can be rigid, semi-rigid, or non-rigid, opaque, semi-opaque or transparent, depending upon the use for which the material is intended. Plastics which have low surface charge when subjected to the electric fields of the present invention and thus which are of particular utility include, for example, polymethylmethacrylate, polycarbonate, polyethylene terepthalate, polystyrene or styrene copolymers, polydimethylsiloxanes, polyurethane, polyvinylchloride, polysulfone, and the like.

In particular embodiments, the devices may include a detector which is positioned to detect agents in the a flow path of the device, e.g., as they move past a defined location or detection region in the flow path. Devices which include an optical or visual detector are generally fabricated, at least in part, from transparent materials to facilitate detection of components within the separation channel by the detector.

The size and shape of the channels or capillaries formed in the substrate of the present devices can have essentially any shape, including, but not limited to, semi-circular, cylindrical, rectangular and trapezoidal. The depth of the channels can vary, but tends to be approximately 10 to 100 microns, and most typically is about 50 microns. The channels tend to be 20 to 200 microns wide.

Manufacturing of the channels and other elements formed in the surface of the substrate can be carried out by any number of microfabricating techniques that are known in the art. For example, lithographic techniques may be employed in fabricating glass or quartz substrates, for example, using established methods in the semiconductor manufacturing industries. Photolithographic masking, plasma or wet etching and other semiconductor processing technologies can be utilized to create microscale elements in and on substrate surfaces. Alternatively, micromachining methods, such as laser drilling, micromilling and the like, can be utilized. Manufacturing techniques for preparing channels and other elements in plastic have also been established. These techniques include injection molding techniques, stamp molding methods, using for example, rolling stamps to produce large sheets of microscale substrates, or polymer microcasting techniques, wherein the substrate is polymerized within a micromachined mold.

Aspects of representative embodiments of the devices of the invention having been described above in general terms, representative device embodiments will now be further described in terms of the figures.

Figure 1:
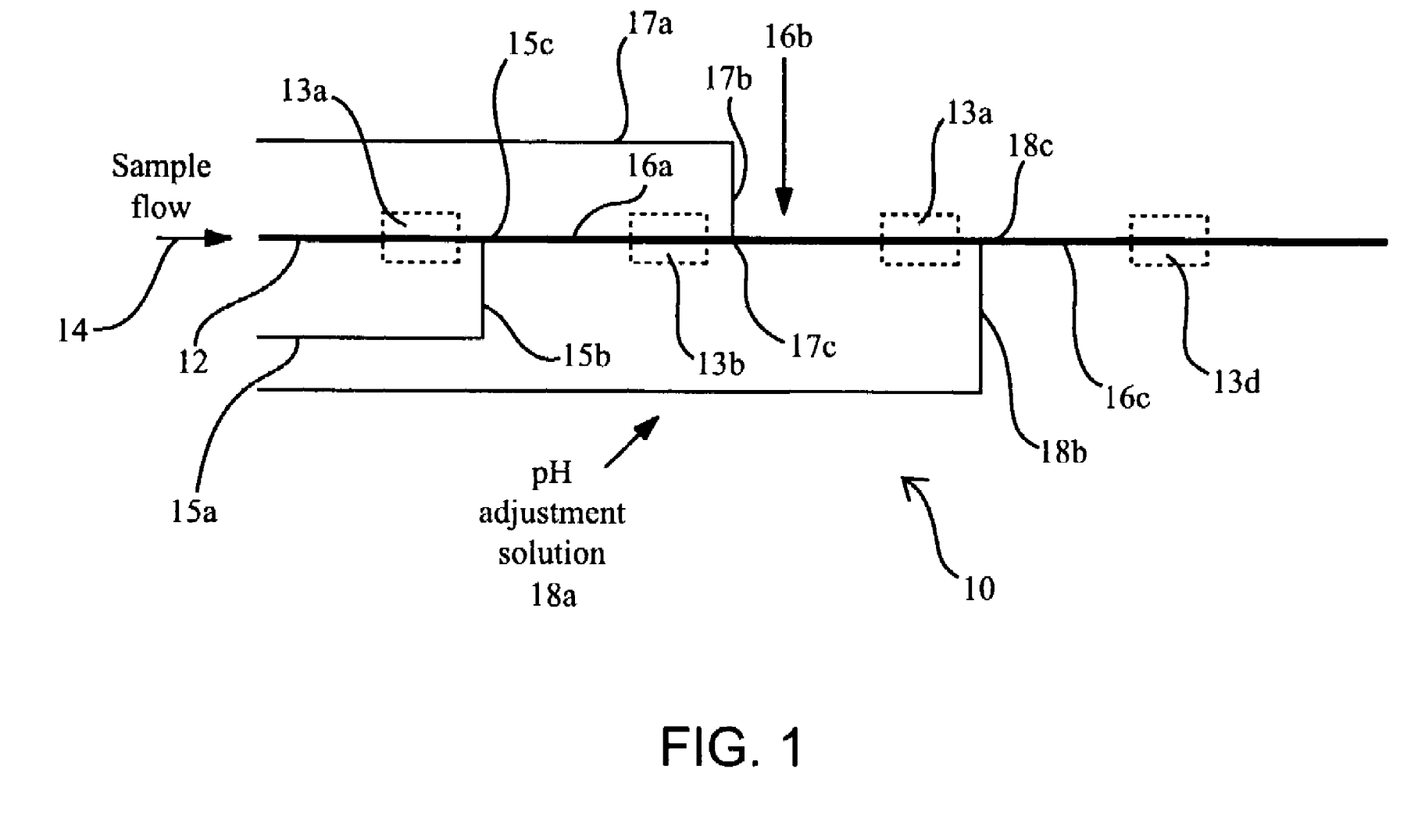
FIG. 1 provides a schematic representation of a device according to a first embodiment of the invention.

FIG. 1 provides a view of a device configured to separate a sample into two or more component fractions based on an isoelectric focusing separation mechanism. In FIG. 1, device 10 includes a central fluid flow path or channel 12. Sample flows along flow path 12 in the direction of arrow 14, e.g., under the influence of an applied pressure. Sequentially positioned along flow path 12 is a plurality of electrophoretic separation elements 13a, 13b, 13c and 13b. Positioned between electrophoretic separation elements 13a and 13b is pH adjustment element 15a. In the embodiment depicted in FIG. 1, pH adjustment element 15a includes a fluid conduit 15b which enters flow path 12 by port 15c. Fluid conduit 15b is in communication with a source of fluid (not shown) of desired pH. Downstream from port 15c is mixing region 16a, which mixing region may include an element for imparting mechanical energy or agitation to fluid present in the flow path in the mixing region 16a, e.g., a stirring mechanism. Positioned between separation elements 13b and 13c is pH adjustment element 17a, which includes conduit 17b and port 17c, as well as mixing region 16b. Positioned between separation elements 13c and 13d is pH adjustment element 18a, which includes conduit 18b and port 18c, as well as mixing region 16c.

Figure 2:
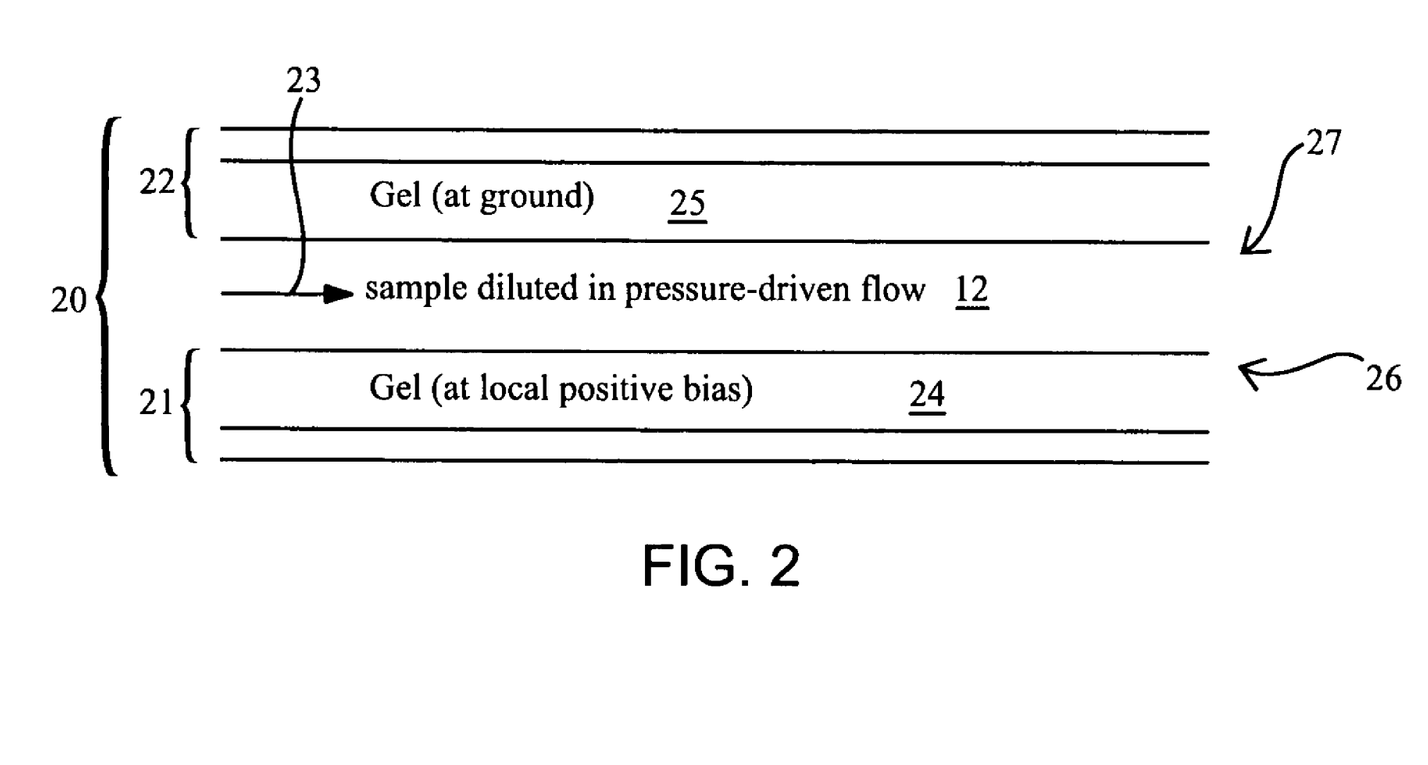
FIG. 2 provides a representation of an electrophoretic separation element of a device according to an embodiment of the invention FIG. 3 provides a schematic representation of a device according to a second embodiment of the invention, where the device is suited for use in two dimensional separation applications.
Figure 3:
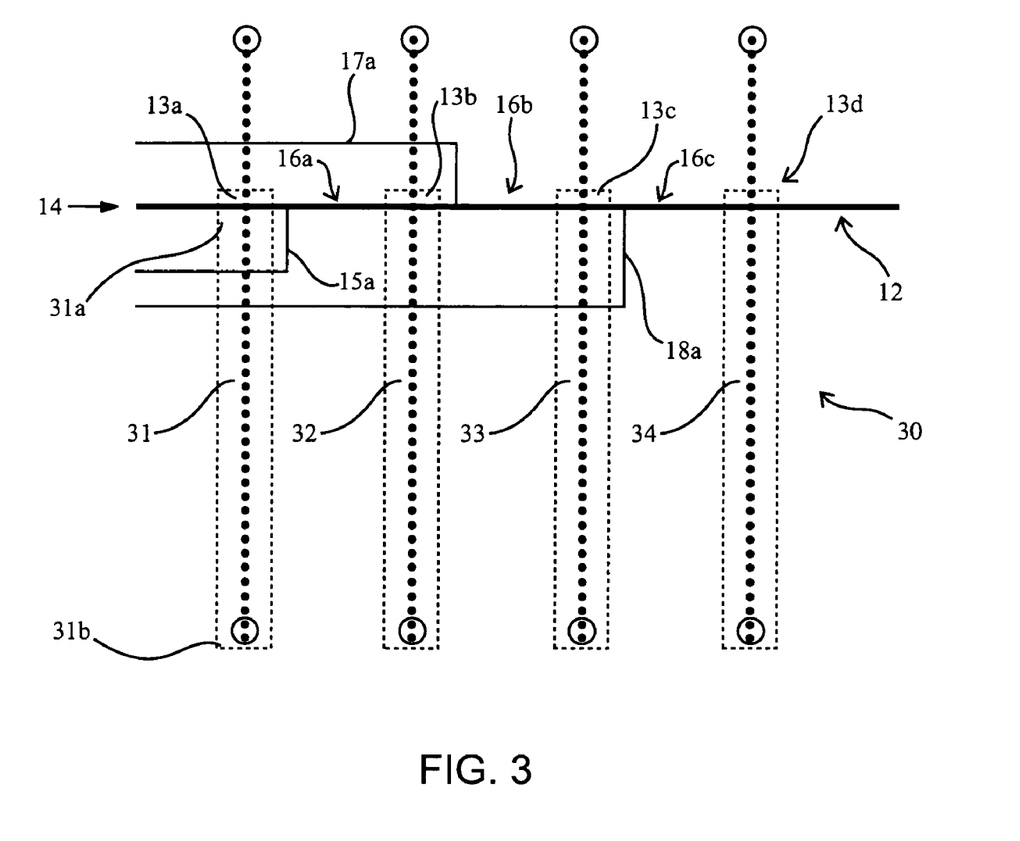

FIG. 2 provides a representation of an electrophoretic separation element of a device according to an embodiment of the invention. In FIG. 2, separation element 20 includes opposing first and second compartments, 21 and 22 respectively, positioned on either side of flow path 12 in which sample flows under pressure influence in the direction of arrow 23. First compartment 21 serves as a trapping element and includes a gel 24 at positive bias, e.g., via a conductive communication with an electrode at positive bias. Gel 24 is separated from flow path 12 by an ion permeable membrane 26 that retains gel 24 in position relative to the flow path and fluid flow therein but is also permeable to proteins, e.g., having dimensions as described above. Second compartment 22 includes gel composition 25 that is separated from flow path 12 by an ion permeable membrane 27 that is impermeable to molecules having a molecule weight that exceeds about 1000 daltons, e.g., about 500 daltons, including about 250 daltons, including proteins, as described above. Gel 25 is maintained at ground or negative bias during use. FIG. 3 provides a schematic representation of a device according to a second embodiment of the invention, where the device is configured to be employed in sample constituent separation protocols in one or two dimensions. In FIG. 3, device 30 includes flow path 12, electrophoretic separation elements 13a, 13b, 13c and 13d, and pH adjustment elements 15a, 17a and 18a, where sample flows along flow path 12 in the direction of arrow 14 under the influence of an applied pressure. Also shown are mixing regions 16a, 16b and 16c.

In FIG. 3, separation element 13a includes trapping element 31 that is an elongated compartment having a size separation gel medium present therein. Trapping element includes at least first and second electrodes 31a and 31b (or leads/conductive elements thereto), positioned at either end for applying an electric field across the size separation medium. Separation elements 13b, 13c and 13d include analogous elongated trapping element compartments 32, 33 and 34, respectively.

Methods

Also provided are methods of electrophoretically separating sample constituents using the subject devices. In certain embodiments of the subject methods is that they include at least a separation of sample constituents based on an isoelectric focusing mechanism. As is known in the art and reviewed above, isoelectric focusing is an electrophoretic method in which zwitterionic substances such as proteins are separated on the basis of their isoelectric points (pI). The pI is the pH at which a zwitterionic species such as a protein has no net charge and therefore does not move when subjected to an electric field. By isoelectric mechanism is meant that the subject methods separate sample constituents using a protocol that uses an entity's isoelectric point or pI to effect separation of the sample components.

In the broadest sense, the subject methods include moving a sample along a flow path, e.g., by applying pressure to the sample to provide for flow of sample along the flow path, past an electrophoretic separation element positioned along the flow path. As the sample moves past the separation element, an electric field is applied between the trapping element of the separation element and a site on a wall of the flow path opposite the trapping element. In representative embodiments, the electric field is applied while sample is moving along the flow path, sample flow along the flow path and application of the electric field across the flow path occurs at the same time or simultaneously. In yet other embodiments, the, movement of sample along the flow path may be stopped while an electric field is applied across the flow path, such that application of the two forces occurs sequentially. In these latter embodiments, following application of an electric field across the flow path, sample may again be moved along the flow path, and then stopped again for application of an electric field across the flow path.

In the applied electric field, the trapping element is typically maintained at a positive bias, and the region of the flow path opposite the trapping element is grounded (or placed at negative bias). As the flow path and trapping element are maintained at a constant pH, sample present in the flow path flowing past the trapping element includes entities bearing a net negative charge, e.g., proteins whose pI is below the pH of the flow path in the separation element. As such, those sample constituents bearing a negative charge migrate out of the flow path into the trapping element in response to the applied electric field, i.e., the negatively charged sample constituents move into the trapping element from the flow path under the influence of the applied electric field. In this manner, constituents of a sample are separated, where the separation mechanism is a pI-based separation mechanism. The fraction of the initial sample that is trapped in the trapping element is conveniently referred to herein as a "pI band", which band is made up of all sample constituents of the sample that have a pI lower than the pH of the electrophoretic separation element past which the sample is moved. When desired, after the remainder of the sample flows past the separation element, the trapped constituents may be released from the trapping element, e.g., by reversing the polarity of the charge bias in the trapping element, such that the trapped components are released. The released constituents may then be obtained from the device for further processing or use, as desired.

In representative embodiments, a device is employed that includes a plurality of electrophoretic separation elements sequentially positioned along a flow path, such as depicted in FIGS. 1 and 3, and described above. When such devices are employed, each sequential electrophoretic separation element can be maintained at a different pH from the remainder of the electrophoretic separation elements positioned along the flow path. In such devices, the sample experiences a plurality of different pH conditions as it moves along the flow path. As a result, a plurality of different pI bands (i.e., constituents of a sample having a pI below the encountered pH at a given separation element) are sequentially extracted from the sample into the respective trapping elements of the electrophoretic separation elements. For example, the method may performed by using a device where the trapping elements are maintained at a positive bias, and the initial pH maintained at the first separation element along the flow path is one that is just slightly above the lowest predicted or known pI of constituents present in the sample to be separated. The remainder of the separation elements along the flow path are maintained at increasing pH values, e.g., by adjusting the pH of the flow path upward along the flow path. As such, a discontinous pH gradient, e.g., a stepwise pH gradient, can be produced in the flow path. As the sample moves down the flow path, each distinct pH value encountered by the sample results in extraction of a separate pI band from the sample. The number of separation elements present in the device can be chosen depending on the desired pI resolution and the expected range of the sample for a given protocol. By adjusting various parameters, e.g., the geometry of the flow path, the electrode dimensions, the flow rates, applied electric fields, etc., a device and protocol can be readily designed to assure substantially complete, if not complete, mobile species depletion of a sample by the time the sample reaches the end of the flow path.

The above methods result in a device in which different fractions or portions of the initial sample, e.g., different pI bands of the initial sample, are trapped in the trapping elements of the sequentially positioned electrophoretic separation elements of the device. In this manner, the sample may be viewed has having undergone an isoelectric focusing separation protocol, where the focusing results in the production of a series of defined fractions or pI bands, as opposed to a continuum of focused entities.

The resultant series of separated sample constituents can be further manipulated as desired. For example, the trapped pI bands may be sequentially released from the trapping elements into the flow channel, and thereby obtained from the flow channel, e.g., for further processing or use. In certain embodiments, the polarity of the trapping element of the first separation element is reversed, while ensuring that an electric field is not present in any of the remaining separation elements, e.g., by grounding the trapping elements in the remaining separation elements, so that the sample constituents present in the first trapping element migrate back into the flow path and then traverse the length of the flow path, e.g., under the influence of applied pressure to the fluid flow path. Following migration of the released constituents of the first trapping element past at least the second separation element, the polarity of the second trapping element can then be changed to force migration of the constituents trapped therein back into the flow path. This process can then be repeated for each sequential separation element along the flow path, such that all of the separated or resolved pI bands of the original sample are recovered.

In certain embodiments, the methods are performed such that following separation of at least one pI band from an initial sample, e.g., using the protocol described above, the resultant pI band that is present in a trapping element is size separated. In such embodiments, once a pI band is present in a given trapping element, an electric field is applied across the medium present in the trapping element that causes the constituents to migrate through the medium, where the medium is a size separation medium, as described above. For example, in a trapping element that includes a size separation gel, the trapping element may include first and second electrodes in conductive communication with the medium at first and second, e.g., top and bottom, locations of the trapping element, such as in the device shown in FIG. 3. Once the pI band is present in the trapping element, e.g., at the top of the trapping element adjacent the flow path, the first electrode may be grounded or have a negative bias applied thereto, while assuring that a positive bias is present at the second electrode. In this manner, an electric field may be applied across the size separation medium present in the trapping element. By assuring that the pH of the medium in the trapping element is present at a value above the pI of the pI band present therein, all the constituents of the pI band will be negatively charged. As a result, the constituents of the pI band will be size separated as the pI band migrates through the size separation medium under the influence of the applied electric field, with the smaller components of the pI band moving faster through the medium than the larger components. As such, the pI band is size separated. Where desired, the size separated components of the initially trapped pI band may then be recovered, e.g., for further use or processing, as desired, e.g., by collected constituents from an outlet well of the trapping element in a manner that is timed to detection of a constituent, e.g., protein, band. In such embodiments, a sample may therefore be subjected to a 2-dimensional size separation protocol, where separation is accomplished based on pi and size.

Depending on the particular protocol employed, fluid withdrawn from the sample flow path or one or more trapping elements of the device can be directed toward a detector for the detection, and even quantitation, of sample constituent(s) e.g., protein(s). This arrangement provides considerable flexibility with regard to the nature of detection and does not limit the methods to the standard gel staining detection techniques common in traditional 2-D gel electrophoresis analysis. The detector need not be positioned to detect eluted proteins. In other arrangements, the detector is adapted so that it can scan resolved proteins within a region of device itself, e.g., along the flow path or in a trapping element. To further enhance detection sensitivity, quantitation and reproducibility, proteins may be labeled at some point prior to detection in certain methods. Depending upon the particular label used, signal-to-noise ratios can be achieved which permit the detection of low abundance proteins.

One or more detectors can be positioned to detect proteins eluting from all or at least multiple trapping elements utilized in the different methods. One suitable arrangement, for example, involves utilizing a UV/VIS detector to detect eluting proteins from early and/or intermediate methods, in part to monitor the amount of protein being collected within a fraction. As such, detectors may be located close to the end of the electrophoretic channels and/or at a position downstream in the main flow channel (e.g., to detect pI bands that are subsequently released into the liquid flow path from the trapping elements). Labeling can then be conducted immediately prior to the final step with subsequent detection of labeled protein from the final capillary. If labeling is conducted at some earlier stage, then a detector (or detectors) can detect labeled protein after all subsequent electrophoretic methods in the series. Also, a staining dye may be employed to facilitate detection.

Proteins can be detected utilizing a variety of methods. One approach is to detect proteins using a UV/VIS spectrometer to detect the natural absorbance by proteins at certain wavelengths (e.g., 214 or 280 nm). In other approaches, proteins in the various fractions can be covalently labeled through a variety of known methods with chromagenic, fluorophoric, or radioisotopic labels. A wide variety of chemical constituents can be used to attach suitable labels to proteins. Chemistries that react with the primary amino groups in proteins (including the N-terminus) include: aryl fluorides, sulfonyl chlorides, cyanates, isothiocyanates, immidoesters, N-hydroxysuccinimidyl esters, chlorocarbonates, carbonylazides, and aldehydes. Examples of chemical constituents that preferentially react with the carboxyl groups of proteins are benzyl halides and carbodiimide, particularly if stabilized using N-hydroxysuccinimide. Both of these carboxyl labeling approaches are expected to label carboxyl containing amino acid residues (e.g., aspartate and glutamate) along with that of the C-terminus. In addition, tyrosine residues can be selectively $^{135}$I-iodinated to allow radiochemical detection.

In some instances, the proteins separated by the methods of the invention are subjected to further analysis. Examples of such methods include infra-red spectroscopy, nuclear magnetic resonance spectroscopy, UV/VIS spectroscopy and complete or partial sequencing. Coupling the current electrophoretic-based method to various mass spectroscopy (MS) methods is one specific example of further analysis that can be conducted. A variety of mass spectral techniques can be utilized including several MS/MS methods and Electrospray-Time of Flight MS methods. Such methods can be used, e.g., to determine at least a partial sequence for proteins resolved by the electrophoretic methods such as a protein sequence tag. In addition, label free detection protocols may be employed, e.g., surface plasmon resonance detection protocols.

The methods of the invention can be used with a wide range of sample types. Essentially any protein-containing sample can be utilized with the methods described herein. The samples can contain a relatively small number of proteins or can contain a large number of proteins, such as all the proteins expressed within a cell or tissue sample, for example.

Samples can be obtained from any organism or can be mixtures of synthetically prepared proteins or combinations thereof. Thus, suitable samples can be obtained, for example, from microorganisms (e.g., viruses, bacteria and fungi), animals (e.g., cows, pigs, horses, sheep, dogs and cats), hominids (e.g., humans, chimpanzees, and monkeys) and plants. The term "subject" as used to define the source of a sample includes all of the foregoing sources, for example. The term "patient" refers to both human and veterinary subjects. The samples can come from tissues or tissue homogenates or fluids of an organism and cells or cell cultures. Thus, for example, samples can be obtained from whole blood, serum, semen, saliva, tears, urine, fecal material, sweat, buccal, skin, spinal fluid, tissue biopsy or necropsy and hair. Samples can also be derived from ex vivo cell cultures, including the growth medium, recombinant cells and cell components. In comparative studies to identify potential drug or drug targets, one sample can be obtained from diseased cells and another sample from non-diseased cells, for example.

Sample preparation for the different electrophoretic techniques, e.g., pI separation, size separation, etc., may be accomplished according to protocols known in the art. If the sample contains cellular debris or other non-protein material that might interfere with separation during electrophoresis, such materials can be removed using any of a variety of known separation techniques including, for example, forcibly exuding the sample through sieve material, filtration and centrifugation. Samples whose ionic strength is particularly high can be desalted using established techniques such as dialysis and dilution and reconcentration.

Where desired, the methods can also include an initial separation by a non-electrophoretic technique prior to commencing the electrophoretic separations. Essentially any type of technique capable of separating proteins can be utilized. Suitable methods include, but are not limited to, fractionation in a sulfate gradient, HPLC, ion exchange chromatography and affinity chromatography.

Programming

Programming for practicing at least certain embodiments of the above-described methods is also provided. For example, algorithms that are capable of controlling one or more aspects of a separation device, e.g., sample introduction, pH modulation, electric field application, etc., are provided. Programming according to the present invention can be recorded on computer readable media, e.g., any medium that can be read and accessed directly or indirectly by a computer. Such media include, but are not limited to: magnetic tape; optical storage such as CD-ROM and DVD; electrical storage media such as RAM and ROM; and hybrids of these categories such as magnetic/optical storage media. One of skill in the art can readily appreciate how any of the presently known computer readable mediums can be used to create a manufacture that includes a recording of the present programming/algorithms for carrying out the above-described methodology.

Utility

The methods and apparatus of the invention can be utilized in a variety of different applications, including applications to detect, characterize and/or identify many sample constituents, and particularly proteins. Consequently, the methods have multiple utilities including, but not limited to, various analytical applications (e.g., monitoring certain protein levels as a function of external stimuli, or detecting specific proteins in complex compositions for identification purposes), clinical applications (e.g., detecting and/or monitoring compositions of normal and diseased cells and tissues, diagnosing or monitoring disease, testing drug candidates for therapeutic efficacy and toxicity testing) and molecular biology and genetic research (e.g., characterizing or monitoring molecular expression levels of gene products and determining the effects of the addition, mutation, deletion or truncation of a particular gene). As such, the methods and apparatus may have utility in proteome research.

In certain applications, the invention can be used in the development of protein databases in which, for example, proteins expressed under particular conditions are isolated, quantified, and identified. For example, the invention can be utilized to determine and catalog a variety of chemical and physical characteristics of resolved proteins of an initial sample, including, but not limited to, pI, and/or apparent molecular weight and/or relative abundance of proteins within a sample. This information can be further cross referenced with a variety of information regarding the source of the sample and the method by which it was collected. Examples of such information include genus, species, age, race, sex, environmental exposure conditions, subject's health, tissue type, method of sample collection and method of sample preparation prior to electrophoresis.

The invention also has value in a variety of comparative studies that can be utilized to identify potential drug targets and/or candidates. For example, the methods can be utilized to identify proteins that are differentially expressed in diseased cells as compared to normal cells. Such differentially expressed proteins can serve as targets for drugs or serve as a potential therapeutic. In a related fashion, the methods can be used in toxicology studies to identify proteins that are differentially expressed in response to particular toxicants. Such differentially expressed proteins can serve as potential targets or as potential antidotes for particular toxic compounds or challenges. The detection and labeling techniques of the invention can facilitate such investigations because these techniques enable even low abundance proteins to be detected and because enhanced reproducibility makes it easier to identify real differences in expression between different samples.

Proteomic studies using certain methods of the invention can detect mutations that result in premature termination of the gene transcript or in amino acid substitutions in the resulting gene product. The methods can also detect post translational modification events associated with disease that are not readily detectable or possible to detect using functional genomics. For example, proteomic methods can detect differences in protein folding, glycosylation patterns, phosphorylation events, and degradation rates.

The results of comparative studies are transferable to a variety of diagnostic applications. For example, the "marker" or "fingerprint" proteins identified during comparative studies as being characteristic of a particular disease can be used to diagnosis individuals to determine if they have the disease correlated with the marker. These markers can also be used in medical screening tests. Once such proteins have been identified, it is not necessary to examine all fractions. Instead, only those fractions potentially containing the marker proteins need be examined. The reproducibility of the methods facilitates such analyses. For systems integrated onto a chip or support, fluid introduction/removal elements can be positioned at the appropriate locations along the separation cavity to withdraw only the relevant fractions potentially containing the marker protein(s) of interest.

As an example of a diagnostic application, proteomic analysis can be utilized in identifying diagnostic markers (e.g., cell surface antigens or serum proteins) for immunodiagnostic assays. Purified samples of putative diagnostic proteins are recovered during proteomic analysis, and can be used to generate antibodies having specific binding affinity to the proteins. Such antibodies can be used to understand the link between the marker protein and the disease through immunological staining to localize the protein in diseased cells or to rapidly screen patients for the presence of the protein, showing its statistical link to the disease.

The methods of the invention have further utility in conducting structure activity studies. For instance, the methods can be used to determine the effect that certain chemical agents or combination of agents have on protein expression patterns. Alterations to the agent or combination can then be made and protein expression reassessed to determine what effect if any the alteration has on protein expression. Such studies can be useful, for example, in making derivatives of a lead compound identified during initial drug screening trials.

Metabolic engineering studies can also be conducted using the methods of the invention. In such studies, a gene can be genetically engineered to include certain changes, or the promoter of a gene can be genetically engineered to increase or decrease the relative expression level of the gene operably linked to the promoter. The methods described herein can then be used to determine what effect, if any, the genetically engineered changes have on proteins other than the protein encoded by the genetically engineered gene.

Kits

Aspects of the invention include kits that find use in sample separation applications, as described above. The kits may include one or more of the components employed in the methods described above, presented in a kit format. Representative components of interest for kits include, but are not limited to: the devices of the invention, e.g., in integrated microfluidic format, programming for interpretation of results, etc. The kits may also include a denaturation reagent for denaturing the analyte, buffers such as hybridization buffers, wash mediums, enzyme substrates, reagents for generating a labeled target sample such as a labeled proteins, negative and positive controls and written instructions for using the devices for carrying out an array based assay.

Aspects of kit embodiments of the invention may also include instructions for use. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or sub packaging), etc. In other embodiments, the instructions are present as an electronic storage data file present on a suitable computer readable storage medium, e.g., CD-ROM, diskette, etc, including the same medium on which the program is presented. In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or World Wide Web. Some form of access security or identification protocol may be used to limit access to those entitled to use the subject invention. As with the instructions, the means for obtaining the instructions and/or programming is generally recorded on a suitable recording medium.

The subject invention provides for a number of distinct advantages in the field of sample, and particularly protein, separation. For example, the devices and methods of the invention can be automated, such that resolved protein fractions are diverted to and collected into specific vessels using pressure and electric forces. This capability provides for reduced error, increased accuracy, and reduced "hands-on" experimental time. The resolved fractions may be recovered in liquid phase, which can simplify downstream processing steps, e.g., extraction and/or recovery steps. The devices are amenable to miniaturization, allowing one to work with small sample sizes, even where samples are complex in nature. As the pH of each separation element can be precisely controlled to a defined value, one can fractionate a sample into precisely defined and narrow pI bands. Furthermore, since the device fractionates a sample into a non-continuous series of pI bands, e.g., by separating according to a non-continuous gradient, samples can be separated in ways not possible using devices that employ continuous pH gradients. As such, the present invention represents a significant contribution to the art.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A device for separating constituents of a sample, said device comprising:
   (a) a fluid flow path;
   (b) two electrophoretic separation elements positioned at spatially separated regions along said fluid flow path, each electrophoretic separation element of said two electrophoretic separation elements comprising:
      (i) an electric field generation element for applying an electric field across the region of said fluid flow path at which said electrophoretic separation element is positioned, wherein said electric field causes charged constituents of said sample to migrate out of said fluid flow path; and
      ii) a trapping element for retaining said charged constituents that have migrated out of said fluid flow path, wherein said trapping element comprises a first compartment separated from said fluid flow path; and
   (c) a pH adjustment element located between said two electrophoretic separation elements, wherein said pH adjustment element changes the pH of fluid in said fluid flow path between said two electrophoretic separation elements.

2. The device according to claim 1, wherein said charged constituents migrate in a direction that is substantially orthogonal to the direction of fluid flow in said fluid flow path.

3. The device according to claim 1, wherein said first compartment is separated from said fluid flow path by an ion permeable barrier.

4. The device according to claim 3, wherein said trapping element further comprises a second compartment separated from said first compartment by said fluid flow path, wherein said second compartment is separated from said fluid flow path by an ion permeable barrier.

5. The device according to claim 1, wherein said pH adjustment element includes a liquid mixing element.

6. The device according to claim 1, wherein said trapping element comprises a gel composition.

7. The device according to claim 6, wherein said gel composition is a size separation gel.

8. The device according to claim 7, wherein said trapping element comprises at least two electrodes for applying an electric field across said size separation gel present in said trapping element.

9. The device according to claim 1, wherein said electric field generation element comprises a first electrode in conductive communication with said trapping element and a second electrode in conductive communication with a site across said fluid flow path from said trapping element.

10. The device according to claim 1, wherein said fluid flow path is a microfluidic flow channel.

11. The device according to claim 1, wherein said device is a microfluidic device.

12. The device according to claim 11, wherein said microfluidic device has an integrated configuration.

13. A method for separating constituents of a sample, said method comprising:
   I. introducing said sample into a fluid flow path of a device comprising:
      (a) two electrophoretic separation elements positioned at spatially separated regions along said fluid flow path, wherein each electrophoretic separation element of said two electrophoretic separation elements comprises:
         (i) an electric field generation element for applying an electric field across the region of said fluid flow path at which said electrophoretic separation element is positioned, wherein said electric field causes charged constituents of said sample to migrate out of said fluid flow path; and
         ii) a trapping element for retaining said charged constituents that have migrated out of said fluid flow path; and
      (b) a pH adjustment element located between said two electrophoretic separation elements, wherein said pH adjustment element changes the pH of fluid in said fluid flow path between said two electrophoretic separation elements; and
   II. moving said sample along said flow path past said two electrophoretic separation elements and applying said electric field across said spatially separated regions of said flow path; and
   III. changing the pH of said sample in said fluid flow path between said two electrophoretic separation elements.

14. The method according to claim 13, wherein said method further comprises releasing trapped constituents of said sample present in said trapping element into said flow path.

15. The method according to claim 13, wherein said method further comprises size separating any constituents trapped in said trapping element.

16. The method according to claim 15, wherein said trapped constituents are size separated by applying an electric field across said trapping element.

17. The method according to claim 13, further comprising collecting at least a portion of said separated sample constituents.

18. A kit comprising:
a device comprising:
(a) a fluid flow path; and
(b) two electrophoretic separation elements positioned at spatially separated regions along said fluid flow path, each electrophoretic separation element of said two electrophoretic separation elements comprising:
 (i) an electric field generation element for applying an electric field across the region of said fluid flow path at which said electrophoretic separation element is positioned, wherein said electric field causes charged constituents of said sample to migrate out of said fluid flow path; and
 ii) a trapping element for retaining said charged constituents that have migrated out of said fluid flow path; and
(c) a pH adjustment element located between said two electrophoretic separation elements, wherein said pH adjustment element changes the pH of fluid in said fluid flow path between said two electrophoretic separation elements.

* * * * *